United States Patent [19]
Fischer

[11] Patent Number: 4,791,220
[45] Date of Patent: Dec. 13, 1988

[54] ISOMERIZATION OF 2-CIS-PENTENOATES TO 2-TRANS-PENTENOATES

[75] Inventor: Rolf Fischer, Heidelberg, Fed. Rep. of Germany

[73] Assignee: BASF Aktiengesellschaft, Ludwigshafen, Fed. Rep. of Germany

[21] Appl. No.: 125,532

[22] Filed: Nov. 25, 1987

[30] Foreign Application Priority Data

Nov. 27, 1986 [DE] Fed. Rep. of Germany ....... 3640598

[51] Int. Cl.$^4$ .................................... C07C 67/333
[52] U.S. Cl. .................................. 560/205; 560/218
[58] Field of Search ............................ 560/205, 218

[56] References Cited

U.S. PATENT DOCUMENTS 4,529,815  7/1985  Schneider et al. ............... 560/205
4,683,341  7/1987  Ishii et al. ........................ 560/218

FOREIGN PATENT DOCUMENTS 133917  11/1977  Japan.
133243  10/1981  Japan.

OTHER PUBLICATIONS

Piva, O., Tetrahedron Lett 27(26), 3001–3004, 1986.
Hine, J. et al., J. Org. Chem 47(14), 2745–2748, 1982.

*Primary Examiner*—Paul J. Killos
*Attorney, Agent, or Firm*—Keil & Weinkauf

[57] ABSTRACT

2-cis-Pentenoates are isomerized to 2-trans-pentenoates by a process in which a 2-cis-pentenoate is treated at from 20° to 250° C. in the presence of one or more compounds of the formula I

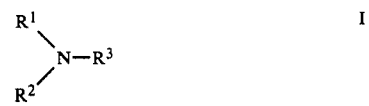

where $R^1$ is hydrogen or $R^1$ and $R^2$ are each cycloalkyl of 5 to 8 carbon atoms or alkyl of 1 to 6 carbon atoms, or $R^1$ and $R^2$ together with the nitrogen atom on which they are substituents may form a 5-membered to 7-membered ring which may additionally contain a further nitrogen or oxygen atom, and $R^3$ is hydrogen or a radical of the formula II

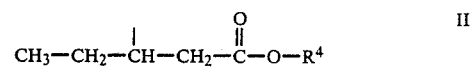

where $R^4$ is alkyl of 1 to 6 carbon atoms, cycloalkyl of 5 to 7 carbon atoms, aralkyl of 7 to 10 carbon atoms or aryl of 6 to 10 carbon atoms, with the proviso that a tertiary amine is present only when $R^3$ is a radical of the formula II.

4 Claims, No Drawings

ISOMERIZATION OF 2-CIS-PENTENOATES TO 2-TRANS-PENTENOATES

According to German Laid-Open Application DOS No. 3,317,163, 2-cis- and 2-trans-pentenoates are obtained as byproducts in the isomerization of 3-pentenoates to 4-pentenoates in the presence of catalysts containing palladium, rhodium or ruthenium. Methyl 2-cis-pentenoate has the same boiling point as methyl 4-pentenoate and therefore cannot be separated from the latter by distillation.

It is an object of the present invention to convert 2-cis-pentenoates to isomers whose boiling point allows them to be separated from 4-pentenoates by distillation, any 4-pentenoate present not being converted.

We have found that this object is achieved by a process for the isomerization of 2-cis-pentenoates to 2-trans-pentenoates, wherein a 2-cis-pentenoate is treated at from 20° to 250° C. in the presence of one or more compounds of the formula I

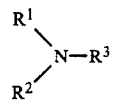

where $R^1$ is hydrogen or $R^1$ and $R^2$ are each alkyl of 1 to 6 carbon atoms or cycloalkyl of 5 to 8 carbon atoms, and $R^1$ and $R^2$ together with the nitrogen atom on which they are substituents may form a 5-membered to 7-membered ring which may additionally contain a further nitrogen or oxygen atom, and $R^3$ is hydrogen or a radical of the formula II

where $R^4$ is alkyl of 1 to 6 carbon atoms, cycloalkyl of 5 to 7 carbon atoms, aralkyl of 7 to 10 carbon atoms or aryl of 6 to 10 carbon atoms, with the proviso that a tertiary amine is present only when $R^3$ is a radical of the formula II.

The novel process has the advantages that 2-cis-pentenoates can be converted in a simple manner to 2-trans-pentenoates, which, because of their boiling point, can readily be separated from the corresponding 4-pentenoates by distillation, and that 4-pentenoates present during the isomerization undergo virtually no conversion.

Preferred 2-cis-pentenoates are derived from alkanols of 1 to 6 carbon atoms, cycloalkanols of 5 to 7 carbon atoms, aralkanols of 7 to 10 carbon atoms or phenol or naphthol. The corresponding alkyl esters have become particularly important, in particular those of alkanols of not more than 3 carbon atoms. Examples of suitable starting compounds are methyl, ethyl, n-propyl, isopropyl, tert-butyl, isobutyl, n-butyl, sec-butyl, n-pentyl, n-hexyl, dodecyl, cyclopentyl, cyclohexyl, cycloheptyl, benzyl, phenylethyl and phenyl 2-cis-pentenoate. The 2-cis-pentenoates may also be present as a mixture with the corresponding 4-, 3-cis- and 3-trans- and/or 2-trans-pentenoates. Typical mixtures contain, for example, from 0.1 to 99.5% by weight of 4-pentenoate, from 0.1 to 99.5% by weight of 3-cis- and trans-pentenoate, from 0.1 to 99.5% by weight of 2-trans-pentenoate and from 0.1 to 100% by weight of 2-cis-pentenoate.

The isomerization is carried out in the presence of one or more compounds of the formula I, where $R^1$ is hydrogen or $R^1$ and $R^2$ are each cycloalkyl of 5 to 8 carbon atoms or alkyl of 1 to 6 carbon atoms, and $R^1$ and $R^2$ together with the nitrogen atom on which they are substituents may form a 5-membered to 7-membered ring which additionally may contain a further nitrogen or oxygen atom, and $R^3$ is hydrogen or a radical of the formula II, where $R^4$ is alkyl of 1 to 6 carbon atoms, cycloalkyl of 5 to 7 carbon atoms, aralkyl of 7 to 10 carbon atoms or aryl of 6 to 10 carbon atoms, with the proviso that a tertiary amine is present only when $R^3$ is a radical of the formula II.

Examples of suitable compounds are primary or secondary amines of the formula I, such as methylamine, ethylamine, n-butylamine, isobutylamine, n-hexylamine, cyclohexylamine, cyclopentylamine, di-n-butylamine or dicyclohexylamine.

In preferred amines of the formula I, $R^3$ is hydrogen and $R^1$ and $R^2$ together with the nitrogen atom on which they are substituents form a 5-membered to 7-membered ring which may additionally contain a nitrogen or oxygen atom. Examples of these are pyrrolidine, piperidine, piperazine, morpholine and hexamethyleneimine.

Other preferred catalysts are tertiary amines of the formula I, where $R^1$ and $R^2$ form a 5-membered or 6-membered ring which may furthermore contain an oxygen or nitrogen atom and $R^3$ is a radical of the formula II, when $R^4$ is, in particular, alkyl of 1 to 6 carbon atoms. Examples of suitable compounds are methyl 3-piperidino-, 3-pyrrolidino-, 3-morpholino- and 3-piperazinovalerate, isopropyl 3-piperidinovalerate, cyclohexyl 3-pyrrolidinovalerate, benzyl 3-piperazinovalerate and phenyl 3-morpholinovalerate.

From 0.01 to 1, in particular from 0.05 to 0.2, mole of the compound of the formula I is advantageously used per mole of 2-cis-pentenoate.

The isomerization is carried out at from 20° to 250° C., in particular from 50° to 200° C., as a rule under atmospheric pressure. However, it is also possible to employ reduced pressure or slightly superatmospheric pressure, for example up to 10 bar. The isomerization is generally effected batchwise or continuously, for example in a homogeneous liquid phase.

Although the isomerization is carried out in general in the absence of solvents, it is also possible to use organic solvents which are inert under the reaction conditions, such as aliphatic or cycloaliphatic hydrocarbons, eg. pentanes, hexanes, cyclohexane, aromatic hydrocarbons, eg. benzene, toluene or xylenes, and ethers, eg. methyl tert-butyl ether, dioxane or tetrahydrofuran, or esters, such as ethyl acetate.

The batchwise isomerization of 2-cis- to 2-transpentenoates is carried out, for example, as follows: the 2-cis-pentenoate, if desired as a mixture with 2-trans-, 3- and/or 4-pentenoates, is heated to the stated temperature together with the abovementioned amount of a compound of the formula I. After a reaction time of, for example, from 0.5 to 5 hours, the catalyst I is separated from the pentenoate isomer mixture, advantageously by distillation. The compound I used as a catalyst can be recycled to the isomerization stage. The pentenoate mixture is, as a rule, then worked up by distillation.

The novel process permits, for example, methyl 2-cis-pentenoate to be converted to methyl 2-trans-pentenoate and thus into a form which can be separated from methyl 4-pentenoate by distillation.

The 2-trans-pentenoates obtainable by the novel process can be isomerized to 3-pentenoates, which are important starting materials for the preparation of adipic acid.

EXAMPLE 1

Isomerization of methyl 2-cis-pentenoate with piperidine in the presence of methyl 2-trans-, 3- and 4-pentenoate A mixture of 2.3 g of methyl 2-cis-pentenoate, 2.3 g of methyl 2-trans-pentenoate, 16 g of methyl 3-pentenoate and 2.3 g of methyl 4-pentenoate (GC: 10.0% by area of methyl 2-cis-pentenoate, 10.4% by area of methyl 2-trans-pentenoate, 67.9% by area of methyl 3-pentenoate and 10.2% by area of methyl 4-pentenoate) was heated with 1.7 g of piperidine for 4 hours at 65° C. Analysis of the pentenoates by gas chromatography (% by area) after this time indicated that the reaction mixture contained 1.0% of methyl 2-cis-pentenoate, 19.5% of methyl 2-trans-pentenoate, 66.5% of methyl 3-pentenoate and 10.1% of methyl 4-pentenoate.

EXAMPLE 2

Isomerization of methyl 2-cis-pentenoate with piperidine in the presence of methyl 4-pentenoate A mixture of 2.3 g of methyl 2-cis-pentenoate and 20.5 g of methyl 4-pentenoate was heated together with 1.7 g of piperidine for 4 hours at 65° C. Analysis (% by area) of the pentenoates by gas chromatography after this time indicated that the reaction mixture contained 0.8% of methyl 2-cis-pentenoate, 9.0% of methyl 2-trans-pentenoate, 0.1% of methyl 3-cis-+trans-pentenoate and 89.8% of methyl 4-pentenoate.

EXAMPLES 3 TO 8

Examples 3 to 8 were carried out as described in Examples 1 and 2. Table 1 contains the starting materials and amounts, reaction conditions and gas chromatographic analyses. 20 g of pentenoate isomer mixture were used in each example.

alpha = 00.65–1.90 m (m, 11 H), 1.90–3.20 (m, 7 H), 3.65 ppm (s, 3 H)

(b) Isomerization of methyl 2-cis-pentenoate with methyl 3-piperidinovalerate in the presence of methyl 4-pentenoate A mixture of 10 g of methyl 2-cis-pentenoate (50%), 10 g of methyl 4-pentenoate (50%) and 1.75 g of methyl 3-piperidinovalerate was heated for 2 hours at 160° C.. Analysis by gas chromatography (% by area) indicated that, after this time, the pentenoate isomer mixture consisted of 4.7% of methyl 2-cis-pentenoate, 44.1% of methyl 2-trans-pentenoate, 1.2% of methyl 3-cis-+trans-pentenoate and 49.3% of methyl 4-pentenoate.

EXAMPLE 10

(a) Preparation of methyl 3-morpholinovalerate

A mixture of 171 g of methyl 2-trans-pentenoate and 130.5 g of morpholine was heated for 46 hours at 100° C. After distillation of the reaction mixture over a Vigreux column, 179 g (59% of theory) of methyl 3-morpholinovalerate of boiling point 85° C./0.4 mbar, $n_D^{20} = 1.4610$, were obtained.

alpha = 00.70–1.80 (m, 5 H), 2.0–3.2 (m, 7 H), 3.45–3.83 (m, 4 H), 3.68 ppm (s. 3 H)

(b) Isomerization of methyl 2-cis-pentenoate in the presence of methyl 4-pentenoate A mixture of 14 g of methyl 2-cis-pentenoate, 6 g of methyl 4-pentenoate and 4.9 g of methyl 3-morpholinovalerate was heated in a glass autoclave for 3 hours at 180° C. After this time, analysis by gas chromatography (% by area) showed that the reaction mixture consisted of 6.6% of methyl 2-cis-pentenoate, 59.9% of methyl 2-transpentenoate and 5.1% of methyl 3-cis- and trans-pentenoate.

EXAMPLE 11

(a) Preparation of methyl 3-piperazinovalerate

A mixture of 213 g of methyl 2-trans-pentenoate and

TABLE 1

| Example No. | PAE mixture[1] used | Catalyst [mol % based on 2-cis-PAE] | Reaction temperature [°C.] | Reaction time [h] | GC [% by area] | | | |
|---|---|---|---|---|---|---|---|---|
| | | | | | 2-cis-PAE | 2-trans-PAE | 3-PAE | 4-PAE |
| 3 | 20% 2-cis-, 80% 4- | n-Hexylamine 10 | 130 | 4 | 8.5 | 11.2 | 0.3 | 78.5 |
| 4 | | Cyclohexylamine 10 | 190 | 3 | 4.4 | 14.0 | 1.9 | 79.3 |
| 5 | 30% 2-cis-, 70% 4- | Piperazine 1 | 180 | 4 | 7.6 | 21.5 | 1.3 | 69.7 |
| 6 | 20% 2-cis-, 80% 4- | Morpholine 5 | 160 | 4 | 7.7 | 12.2 | 0.3 | 79.3 |
| 7 | | Pyrrolidine 5 | 160 | 2 | 2.6 | 16.7 | 0.8 | 79.2 |
| 8 | 30% 2-cis-, 70% 4- | Di-n-butylamine 10 | 140 | 4 | 20.7 | 6.9 | 2.5 | 69.8 |

[1]PAE = methyl pentenoate

EXAMPLE 9

(a) Preparation of methyl 3-piperidinovalerate

A mixture of 500 g of methyl 2-trans-pentenoate and 372 g of piperidine was heated at 65° C. for 17 hours and then at 100° C. for 24 hours. After distillation over a Vigreux column, 562 g (64% of theory) of methyl 3-piperidinovalerate of boiling point 64° C./2 mbar, $n_D^{20} = 1.4592$, were obtained.

64 g of piperazine was stirred for 44 hours at 60° C. Fractional distillation gave 77.1 g of methyl 3-piperazinovalerate of boiling point 105° C./0.4 mbar, $n_D^{20} = 1.4740$, the yield being 51%, based on piperazine used. delta = 0.70–1.80 (m, 5 H), 1.72 (s, 1 H), 2.0–3.2 (m, 11 H), 3.70 ppm (s, 3 H).

(b) Isomerization of methyl 2-cis-pentenoate

A mixture of 15 g of methyl 2-cis-pentenoate and 2.6 g of methyl 3-piperazinovalerate was heated for 4 hours at 130° C. After this reaction time, analysis by gas chromatography indicated that the reaction mixture consisted of 5% of methyl 2-cis-pentenoate, 91% of methyl 2-transpentenoate and 4% of methyl 3-cis- and transpentenoate.

(c) Isomerization of methyl 2-cis-pentenoate in the presence of methyl 4-pentenoate A mixture of 10 g of ethyl 2-cis-pentenoate, 10 g of methyl 4-pentenoate and 1.75 g of methyl 3-piperazinovalerate was heated for 4 hours at 130° C. After this time, analysis by gas chromatography indicated that the reaction mixture consisted of 3.9% of methyl 2-cis-pentenoate, 45% of ethyl 2-trans-pentenoate, 1.4% of methyl 3-cis- +trans-pentenoate and 49.5% of methyl 4-pentenoate.

EXAMPLE 12

(a) Preparation of methyl 3-pyrrolidinovalerate

A mixture of 171 g of methyl 2-trans-pentenoate and 106.5 g of pyrrolidine was heated for 20 hours at 100° C. After distillation over a Vigreux column, 198.7 g (72% of theory) of methyl 3-pyrrolidinovalerate of boiling point 65° C./0.4 mbar, $n_D^{20} = 1.4580$, were obtained.

delta=0.89 (t, 3 H), 1.20–2.0 (m, 6 H), 2.10–3.10 (m, 7 H), 3.65 ppm (s, 3 H)

(b) Isomerization of methyl 2-cis-pentenoate

A mixture of 15 g of methyl 2-cis-pentenoate and 2.4 g of methyl 3-pyrrolidinovalerate was heated for 0.5 hour at 180° C. in a glass autoclave. After this time, analysis by gas chromatography indicated that the reaction mixture consisted of 32% of methyl 2-cis-pentenoate, 65% of methyl 2-trans-pentenoate and 4% of methyl 3-cis- +trans-pentenoate.

I claim:

1. A process for the isomerization of 2-cis-pentenoates to 2-trans-pentenoates, wherein a 2-cis-pentenoate is treated at from 20 to 250° C. with from 0.1 to 1 mole, per mole of 2-cis-pentenoate, of one or more compounds of the formula I

where $R^1$ is hydrogen or $R^1$ and $R^2$ are each cycloalkyl of 5 to 8 carbon atoms or alkyl of 1 to 6 carbon atoms, or $R^1$ and $R^2$ together with the nitrogen atom on which they are substituents may form a 5-membered to 7-membered ring which may additionally contain a further nitrogen or oxygen atom, and $R^3$ is hydrogen or a radical of the formula II

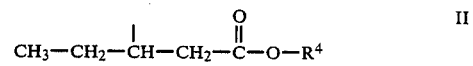

where $R^4$ is alkyl of 1 to 6 carbon atoms, cycloalkyl of 5 to 7 carbon atoms, aralkyl of 7 to 10 carbon atoms or aryl of 6 to 10 carbon atoms, with the proviso that the tertiary amine is present only when $R^3$ is the radical of the formula II.

2. A process as claimed in claim 1, wherein piperidine, pyrrolidine, morpholine or piperazine is used as the compound of the formula I.

3. A process as claimed in claim 1, wherein a 3-piperidino-, 3-pyrrolidino-, 3-morpholino- or 3-piperazinovalerate is used as the compound of the formula I.

4. A process as claimed in claim 1, wherein from 0.05 to 0.2 mole of a compound of the formula I is used per mole of 2-cis-pentenoate.

* * * * *